(12) United States Patent
Gherardi

(10) Patent No.: US 7,741,051 B2
(45) Date of Patent: Jun. 22, 2010

(54) SOLUBLE ECTODOMAIN FRAGMENTS OF MET AND USES THEREOF

(75) Inventor: Ermanno Gherardi, Cambridge (GB)

(73) Assignee: Medical Research Council, London (GB)

( * ) Notice: Subject to any disclaimer, the term of this patent is extended or adjusted under 35 U.S.C. 154(b) by 177 days.

(21) Appl. No.: 10/571,943

(22) PCT Filed: Sep. 15, 2004

(86) PCT No.: PCT/GB2004/003957

§ 371 (c)(1),
(2), (4) Date: Jul. 18, 2006

(87) PCT Pub. No.: WO2005/026361

PCT Pub. Date: Mar. 24, 2005

(65) Prior Publication Data

US 2007/0037209 A1    Feb. 15, 2007

(30) Foreign Application Priority Data

Sep. 15, 2003  (GB) ................. 0321630.6

(51) Int. Cl.
*G01N 33/53* (2006.01)
*A61K 38/16* (2006.01)
*C07K 14/00* (2006.01)

(52) U.S. Cl. .................. 435/7.1; 530/300; 530/350

(58) Field of Classification Search .............. 435/69.1
See application file for complete search history.

(56) References Cited

U.S. PATENT DOCUMENTS 5,871,959 A    2/1999   Tsarfaty et al.

OTHER PUBLICATIONS

Prat, M., et al. 1991 Molecular and Cellular Biology 11(12): 5954-5962.*
Bottaro, D.P., et al. 1991 Science 251: 802-804.*
Naldini, L., et al. 1991 Oncogene 6: 501-504.*
Naldini, L, et al. 1991 The EMGO Journal 10: 2867-2878.*
International Search Report for PCT/GB2004/003957 dated Nov. 29, 2004.
Mark et al., *Expression and characterization of hepatocyte growth factor receptor-IgG fusion proteins*, Journal of Biological Chemistry, vol. 267, No. 36, Dec. 25, 1992, pp. 26166-26171, XP002106575.
Database GNESEQ, CHICZ RM: *Human expressed protein tag (EPT)* #649, XP002305675.
Chirgadze et al., *Insights into the structure of hepatocyte growth factor/scatter factor (HGF/SF) and implications for receptor activation*, FEBS Letters, vol. 430, No. 1-2, Jun. 23, 1998, pp. 126-129, XP004259150.
Gherardi et al., *Functional map and domain structure of MET, the product of the c-met protooncogene and receptor for hepatocyte growth factor/scatter factor*, Proceedings of the National Academy of Sciences, Oct. 14, 2003, vol. 100, No. 21, pp. 12039-12044, XP002305673.
Kong-Beltran et al., *The Sema domain of Met is necessary for receptor dimerization and activation*, Cancer Cell, vol. 6, No. 1, Jul. 2004, pp. 75-84, XP002305674.
Hoshino et al, "Expression of the hepatocyte growth factor receptor in the regenerating rat liver", Cancer Letters, 71 (1993) 119-123.
NCBI Accession No. P14210, version P14210.2, Aug. 1, 1991 (www.ncbi.nlm.nih.gov—printed Feb. 10, 2008).
NCBI Accession No. P08581, version P08581.3, Dec. 1, 1992 (www.ncbi.nlm.nih.gov—printed Feb. 10, 2008).

* cited by examiner

*Primary Examiner*—Manjunath N Rao
*Assistant Examiner*—Marsha M Tsay
(74) *Attorney, Agent, or Firm*—Nixon & Vanderhye P.C.

(57) ABSTRACT

The invention relates a fragment derived from the MET ectodomain which the inventors have found is capable, in monomer form, of binding to HGF/SF either in the presence or absence of heparin. The availability of soluble, monomeric forms of the MET receptor enabled studies of its solution properties and HGF/SF binding and provides an assay comprising the steps of (a) providing a MET ectodomain fragment; (b) providing an agent; and (c) determining the extent to which the agent interacts with said fragment.

13 Claims, 7 Drawing Sheets

SEQUENCE LISTING

<160> NUMBER OF SEQ ID NOS: 2

<210> SEQ ID NO 1
<211> LENGTH: 1390
<212> TYPE: PRT
<213> ORGANISM: Homo sapiens

<400> SEQUENCE: 1

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350
```

```
Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
        420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
        500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
        580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
        660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
        740                 745                 750

Phe Ile Ser Gly Gly Ser Thr Ile Thr Gly Val Gly Lys Asn Leu Asn
        755                 760                 765
```

```
Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser  Val Asp Tyr Arg Ala  Thr Phe Pro
            995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser  Pro Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095

Asp Asn  Asp Gly Lys Lys Ile  His Cys Ala Val Lys  Ser Leu Asn
    1100                1105                1110

Arg Ile  Thr Asp Ile Gly Glu  Val Ser Gln Phe Leu  Thr Glu Gly
    1115                1120                1125

Ile Ile  Met Lys Asp Phe Ser  His Pro Asn Val Leu  Ser Leu Leu
    1130                1135                1140

Gly Ile  Cys Leu Arg Ser Glu  Gly Ser Pro Leu Val  Val Leu Pro
    1145                1150                1155

Tyr Met  Lys His Gly Asp Leu  Arg Asn Phe Ile Arg  Asn Glu Thr
    1160                1165                1170
```

```
His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140
```

-continued

```
Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560
```

-continued

```
Cys Lys Gln Val Leu Asn Val Ser Gln Leu Val Tyr Gly Pro Glu Gly
            565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

SOLUBLE ECTODOMAIN FRAGMENTS OF MET AND USES THEREOF

This application is the US national phase of international application PCT/GB2004/003957 filed 15 Sep. 2004, which designated the U.S. and claims priority to GB 0321630.6 filed 15 Sep. 2003, the entire content of each of which is hereby incorporated by reference.

FIELD OF THE INVENTION

The present invention relates to monomeric protein fragments derived from the ectodomain of the MET receptor.

BACKGROUND TO THE INVENTION

Receptor tyrosine kinases (RTKs) mediate intercellular signals essential for the development and maintenance of the cells of multicellular organisms. The minimal domain structure of RTKs consists of an extracellular ligand-binding domain, a single transmembrane helix and a cytoplasmic kinase domain. This minimal structure, however, is very rare and typically the extracellular moiety of RTKs, the ectodomain, consists of complex and distinctive domain sets which enable classification of the RTKs in different families (1).

There is a strong preference for certain domains to occur in the ectodomain of RTKs. The fibronectin type-3 (FN-3) domain, for example, is present as 2 copies in the large Eph receptor family, 3 copies in the insulin and IGF-1 receptors and at least 7 copies in the ROS receptor (1). Cysteine-rich domains of variable length are also commonly found in RTKs.

A large number of RTKs contain immunoglobulin (IG) domains and the ectodomain of certain families consists solely of IG domains: the FGF receptors contain 2 or 3, depending on RNA splicing, the PDGF, CSF1, KIT and FLK2/STK1 receptors contain 5 and the FLT1, FLK1, FLT4 and CCK4 receptors contain 7 (1). IG domains can also be present in combination with FN-3, cysteine-rich or other domains (1). Interestingly, most IG domains present in RTKs and cell adhesion molecules belong to a distinct structural set known as the 'I set', with architecture intermediate between the V and C1 sets (2).

MET, the RTK encoded by the c-met proto-oncogene (3, 4), is the receptor for HGF/SF (5) a large polypeptide growth factor discovered as a protein causing dispersion of epithelial colonies and cell migration (scatter factor) (6, 7) and as a liver mitogen (hepatocyte growth factor) (8-10). HGF/SF and MET are essential for the development of several tissues and organs including, the placenta (11, 12), liver (11), and several groups of skeletal muscle (13). They also play a major role in the abnormal migration of cancer cells as a result of overexpression or MET mutations (14). In contrast to extensive data on the signal transduction pathways activated by MET (15), little is known about extracellular MET.

The involvement of MET in the spread of tumours makes this gene a suitable target for the development of antagonists which might prevent the activation of this RTK. The development of suitable assays involving large complex proteins can be difficult, particularly where is it desired to have a robust process suitable for high-throughput screens. This can be particularly problematical where, as with MET, receptor dimerization is believed to be required for binding to its cognate ligand.

Mark et al, J. Biol. Chem. 1992, 267; 26166-26171, describe fusions of the extracellular domain of the MET receptor to the constant region of an IgG heavy chain. These fusions produce soluble met protein which forms a dimer through the presence of the heavy chain region.

DISCLOSURE OF THE INVENTION

We have investigated the properties of the MET receptor and found that surprisingly a fragment derived from the MET ectodomain in monomer form binds to HGF/SF either in the presence or absence of heparin. The availability of soluble, monomeric forms of the MET receptor enabled studies of its solution properties and HGF/SF binding.

Accordingly, the present invention provides an assay method which comprises:

(a) providing a MET ectodomain fragment;
(b) providing an agent; and
(c) determining the extent to which the agent interacts with said fragment.

Interaction of the ectodomain fragment with the agent includes binding of said agent to said fragment, disrupting the dimerization of said fragment, disrupting the ability of said fragment to bind to HGF/SF or a fragment thereof which binds to said ectodomain, or disrupting the ability of the fragment to bind to heparin or heparan sulphate.

In a preferred embodiment, the assay is performed in the presence of HGF/SF or a fragment thereof which binds to said ectodomain.

In a further aspect, the assay of the invention may be performed in the presence of heparin or heparan sulfate.

The assay may be performed in any convenient format, for example in solution or wherein one of the components is on a solid support.

The invention further provides an isolated protein which consists of a MET ectodomain fragment.

The invention also provides a composition comprising MET ectodomain fragment proteins of the invention.

DETAILED DESCRIPTION OF THE INVENTION

MET Protein

Figure 1:
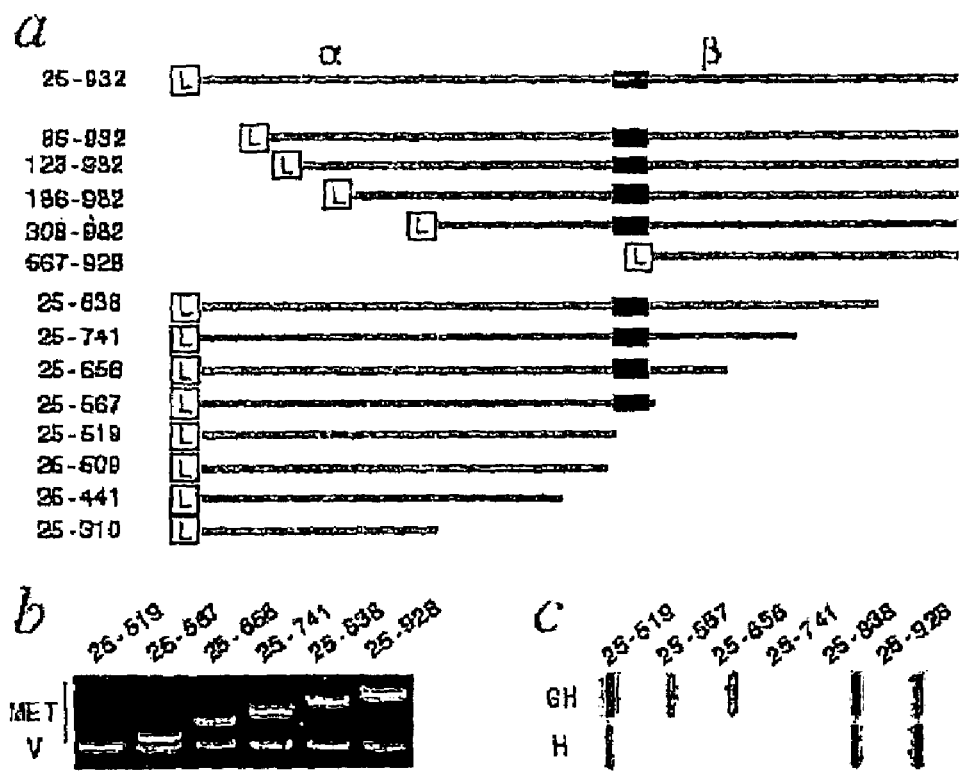
FIG. 1 shows deletion mapping and expression of MET domains. a. Schematic view and sequence boundaries of N- and C-terminal deletions of the MET ectodomain. The alpha and beta chains are shown in different shades of grey. L indicates a 21 aa immunoglobulin leader used for secretion of MET proteins and the black box corresponds to the cysteine-rich sequence (aa 520-561) of the MET beta chain. The cDNAs corresponding to several C-terminal deletions of the MET ectodomain (top bands, M) are shown along with a vector band (V). c. Expression of the same MET deletions in supernatants of stable transfectants of the mouse myeloma line NS0. H and GH define monomeric and dimeric MET constructs respectively.

The sequence of the MET protein is available as SwissProt accession number P08581 (SEQ ID NO:1). The numbering used herein refers to the numbering of this protein, with residue 1 being the translation start site.

A MET ectodomain fragment is defined as a protein corresponding to the MET amino acid residues 25-928 or an N-terminal fragment thereof. The N-terminal fragment preferably comprises at least 495, for example about 600 or 700 amino acids. In one embodiment the fragment is the region 25-519.

The MET sequence may be that of the wild-type human sequence of SwissProt accession number P08581. However, it may also be an allelic variant such as the A320V variant.

The MET sequence may also be a variant of the human MET sequence having at least 70%, preferably at least 80%, more preferably at least 90%, such as at least 95% for example at least 98% sequence identity to wild-type human MET. The percentage identity of amino acid sequences can be calculated using commercially available algorithms. The programs (provided by the National Center for Biotechnology Information) protein-protein BLAST or BLAST2 Sequences may be used to determine identities of sequences using default parameters.

The variant will retain the ability to bind at least HGF/SF and preferably also heparin.

The MET ectodomain fragment will consist essentially of the N-terminal regions defined above, though this fragment may additionally comprise, at its N-terminal and/or its C-terminal, short sequences of no more than 40 amino acids of non-MET sequences which facilitate expression, recovery or detection of the fragment. Such sequences include, at the N-terminus, leader sequences and, at either terminus, tags such as a hexahistidine tag.

HGF/SF

The hepatocyte growth factor HSF/SF is a pleiotropic growth factor that stimulates cell growth, cell motility, morphogenesis and angiogenesis. HGF/SF is produced as an inactive monomer (of about 100 kDa) which is proteolytically converted to its active form. Active HGF/SF is a heparin-binding heterodimeric protein composed of a 62 kDa alpha-chain and a 34 kDa beta-chain. The sequence of human wild type HGF/SF is recorded as SwissProt reference P14210 (SEQ ID NO:2).

Fragments of HGF/SF are also known to be active in binding to MET, and such fragments may also be used. HGF/SF has a unique domain structure that resembles that of the blood proteinase precursor plasminogen and consists of six domains: an N-terminal (N) domain, homologous to plasminogen activation peptide, four copies of the kringle (K) domain and a catalytically inactive serine proteinase domain. Two products of alternative splicing of the primary HGF/SF transcript encode NK1, a fragment containing the N and the first K domain, K1 (53), and NK2, a fragment containing the N, K1 and second kringle, K2, domains (54, 55). Experiments in transgenic mice have subsequently indicated that NK1 behaves in vivo as a bona fide receptor agonist (56).

Accordingly, reference herein to the use of HGF/SF in assays of the present invention includes the use of fragments active in binding MET including the NK1 and NK2 fragments.

Variants of HGF/SF and its fragments which also retain MET binding activity may be used. Such variants may have at least 70%, preferably at least 80%, more preferably at least 90%, such as at least 95% for example at least 98% sequence identity to wild-type human HGF/SF or fragment thereof. The percentage identity of amino acid sequences can be calculated using commercially available algorithms as indicated in the preceding section.

Heparin and Heparan Sulphate

Heparin is a heterogenous group of highly sulfated, straight-chain anionic mucopolysaccharides, called glycosaminoglycans. The molecular weight of heparin varies from about 6,000 to about 20,000 Da depending on the source and the method of determination. Heparan sulfate is a sulfated polysaccharide structurally similar to heparin. Heparan sulfate, found in cell surface proteoglycans, has a similar structure to heparin, although it is typically less extensively suflated than heparin. Extensive heterogeneity exists in heparan sulfates—including the length of the saccharide chain, the extent of sulfation and the core carbohydrate sequence. Heparin, heparin salts (heparin sodium) and heparan sulfate are commercially available.

Agents

The assay of the present invention may be used to determine the binding of a wide variety of agents to the MET protein. An agent is any compound or substance (e.g. mixture of compounds) for which it is desired to determine its binding to the MET protein. Agents include proteins, peptides, small molecules which may be obtained from combinatorial libraries, plant extracts and the like. Proteins include antibodies and fragments thereof retaining at least the antibody heavy chain variable domain (VH domain), preferably in association with a light chain variable domain (VL domain). The fragment may be for example a Fv, scFv or Fab fragment.

Assays of the Invention

Assays according to the invention may be performed in any suitable format convenient to the person of ordinary skill in the art.

As indicated above, the assays of the invention may be configured to examine the ability of an agent to bind to the MET ectodomain, or the ability of the domain to bind, in the presence of the agent, to HGF/SF, fragments thereof, heparin or heparan sulfate.

For example, the MET ectodomain fragment may be attached to a solid support, such as a column or bead. Attachment may be achieved via a tag such as a six-his tag which can be used to bind the protein to a nickel chelate. The agent and where applicable other components may be brought into contact with the MET ectodomain and the amount of agent bound can be determined.

In one embodiment of this assay, the agent is brought into contact with the MET ectodomain fragment in the presence of HGF/SF or a fragment thereof which (in the absence of the agent) binds to the ectodomain. The agent and HGF/SF may be added simultaneously or sequentially in either order. The amount of HGF/SF bound to the ectodomain may be determined, and the effect of binding caused by the agent (e.g. antagonism) may be examined.

The binding of HGF/SF may be determined by any suitable means. For example, it can be detected in an ELISA-type assay method. Such a method may for example involve using a first antibody against HGF/SF to bind the HGF/SF in the sample, and a second, enzyme-linked, antibody directed against the first antibody. Alternatively, the HGF/SF (or fragment thereof) or first antibody may be labelled directly with a detectable label. Such a label includes an enzyme (e.g. horse radish peroxidase, (HRP)), a fluorescent label (e.g. green fluorescent protein) or an affinity label such as biotin.

Alternatively or in addition, the agent may for example be labelled, e.g. with a fluorescent or radio-label in order to facilitate detection and monitoring.

An agent which is found to bind to MET in accordance with the assay of the invention may be investigated further. For example, the ability of the agent to affect dimerization of the MET protein (or a dimerizing form thereof, such as the antibody heavy chain linked ectodomain) may be examined by using gel electrophoresis (e.g. native polyacrylamide gel electro-phoresis), gel filtration or ultracentrifugation. As illustrated in the accompanying examples, the dimer form of the MET ectodomain can be detected by such methods, and thus the effect of the agent on the formation of the dimer, or the interaction of the dimer with HGF/SF and/or heparin or heparan sulphate can be examined.

Furthermore, it may be manufactured and/or used in preparation, i.e. manufacture or formulation, of a composition such as a medicament, pharmaceutical composition or drug. These may be administered to individuals, e.g. for any of the purposes discussed elsewhere herein.

In a further aspect, the present invention provides the use of an agent identified or obtained using an assay in accordance with the present invention in methods of designing or screening for mimetics of the agent. Thus the invention provides comprises performing an assay according to the invention to obtain an agent, identifying in the agent a pharmacophore and modelling the pharmacophore to design further compounds having increased binding activity.

Where the agent is a peptide, the invention provides a method of designing mimetics. of a peptidyl substance able to bind the MET ectodomain identified or obtained using an assay as disclosed herein, said method comprising: (i) analysing the agent to determine the amino acid residues essential and important for the binding activity to define a pharmacophore; and, (ii) modelling the pharmacophore to design and/or screen candidate mimetics having the binding activity.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

Once the pharmacophore has been found, its structure is modelled according to its physical properties, e.g. stereochemistry, bonding, size and/or charge, using data from a range of sources, e.g. spectroscopic techniques, X-ray diffraction data and NMR.

Computational analysis, similarity mapping (which models the charge and/or volume of a pharmacophore, rather than the bonding between atoms) and other techniques can be used in this modelling process. A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

Generally, such an agent obtained according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. A composition according to the present invention may include in addition to the agent one or more other molecules of therapeutic use, such as an anti-tumour compounds.

The present invention extends in various aspects not only to an agent identified as binding to the MET ectodomain, but also a pharmaceutical composition, medicament, drug or other composition comprising such an agent. An agent obtained according to the present invention may be provided for use in a method of treatment of the human or animal body by therapy which affects the growth or spread of tumour cells. Administration of the agent will be of a therapeutically effective amount this being sufficient to show benefit to the individual.

The agent may be administered in a localised manner to a tumour site or other desired site or may be delivered in a manner in which it targets tumour or other cells.

Isolated MET Ectodomain Fragment

In another aspect, the present invention relates to an isolated MET ectodomain fragment. Isolated fragments of the invention will be those as defined above in isolated form, free or substantially free of material with which the native MET protein is naturally associated such as other polypeptides with which it is found in the cell. The fragments may of course be formulated with diluents or adjuvants and still for practical purposes be isolated. The fragments may be glycosylated, either naturally or by systems of heterologous eukaryotic cells, or they may be (for example if produced by expression in a prokaryotic cell) unglycosylated. Fragments may phosphorylated and/or acetylated.

A isolated MET ectodomain fragment of the invention may also be in a substantially purified form, in which case it will generally comprise the fragment in a preparation in which more than 90%, e.g. 95%, 98% or 99% of the detectable protein in the preparation is a MET ectodomain of the invention.

Compositions

In another aspect, the invention provides a MET ectodomain fragment composition. Such a composition may comprise the ectodomain in a suitable carrier or diluent, e.g. a buffer comprising phosphate (e.g. 20-100 mM phosphate) and/or salt (e.g. 10-200 mM NaCl) at a pH from 6.0 to 8.0.

The compositions may comprise any suitable concentration of protein, typically from $10^{-10}$ to $10^{-5}$ M, preferably about $10^{-8}$ M.

The composition optionally may contain HGF/SF or a fragment thereof which binds to said ectodomain. Such fragments particularly include the NK1 and NK2 fragments. The HGF/SF or fragment thereof may be present at a concentration of $10^{-11}$ to $10^{-7}$ M, preferably about $10^{-6}$ M. Desirably the molar ratio of the ectodomain and HGF/SF (or fragment thereof) will be about 1:1, and usually within the range of from 2:1 to 1:2.

The composition may contain heparin or heparan sulfate (or mixtures thereof). When present the heparin or heparan sulfate may be at a concentration of $10^{-8}$ to $10^{-4}$ M, preferably about $10^{-6}$ M. Desirably the molar ratio of the ectodomain and heparin (or heparan sulfate) will be about 1:1, and usually within the range of from 2:1 to 1:2.

In a preferred aspect, the composition comprises both (a) HGF/SF or a fragment thereof and (b) heparin or heparan sulfate, both at the concentration ratios discussed above. Most desirably the concentration ratios and 1:1:1 for the ectodomain fragment and (a) and (b).

Use of MET Ectodomains

Compositions of the invention comprising a MET ectodomain may be used in an in vitro or in vivo method to antagonise the binding of the HGF/SF ligand to the MET receptor located on the surface of a cell. Such antagonism may be useful for the treatment of conditions where cells are proliferating or migrating at least in part by the activation of the MET receptor, e.g. as a result of over-expression or mutation of this receptor.

Thus the invention provides the use of a MET ectodomain fragment of the invention, or composition thereof, in a method of treating unwanted cellular proliferation or migration in a human or animal subject. Such unwanted proliferation or migration includes disease such as cancer, particularly glioblastomas, carcinomas and sarcomas.

In such methods, the MET ectodomain or compositions thereof as defined above may be administered by any suitable route, e.g. by injection such as intravenous or intraarterial injection, or directly to the site of the tumour. Doses will be selected by the physician according to the state of the subject, though generally doses of about 0.1 to 1.0 mg/kg might be suitable.

The following examples illustrate the invention.

EXAMPLE 1

Materials and Methods

Expression and Purification of MET proteins.

Two silent mutations were introduced in codons $Q_{559}$ and $I_{560}$ of a full length human MET cDNA to remove a Bgl II site. MET deletions lacking the endogenous leader (aa 1-24) were generated by PCR as Mlu I-Bgl II inserts. For monomeric MET proteins, inserts were cloned in frame between a 21 aa IG leader and a hexa-histidine sequence. For dimeric proteins, inserts were cloned between the same IG leader and the hinge, $CH_2$ and $CH_3$ domains of the human γ1 antibody constant region gene followed by a hexa-histidine sequence. These contructs cause MET dimerisation through the antibody (Fc) portion. For expression, MET constructs in plasmid pA71d were transfected in the mouse myeloma line NS0 or in Lec 8 cells (16). Stable transfectants were selected in 0.75 mg/ml hygromycin, screened for expression and positive cultures were cloned and expanded for protein production. Monomeric MET proteins were purified on a Ni-NTA Agarose column (Qiagen MG3398) and eluted with 0.4 M imidazole followed by further purification on Mono S columns (Amersham Biosciences 17-0547-01). Purification of dimeric MET proteins was carried out on Ni-NTA Agarose followed by chromatography on Protein A Sepharose CL-4B (Amersham Biosciences 17-0780-01).

Binding Assays.

Figure 2:
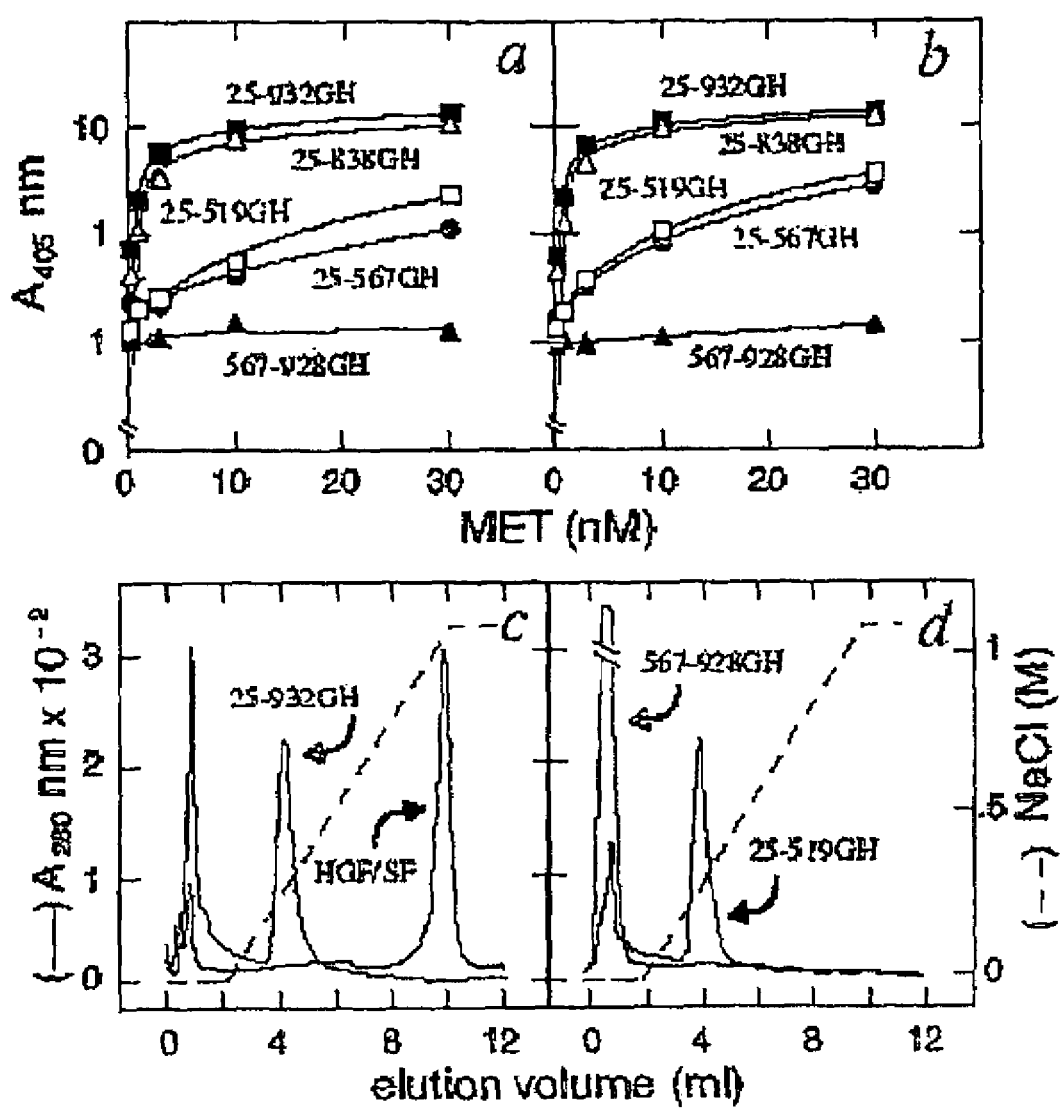
FIG. 2 shows binding of MET deletions to HGF/SF (a and b) or heparin (c and d). a and b. Binding of MET deletions to single chain (a) or two chain (b) HGF/SF as measured in a solid phase assay. c and d. Binding of three MET constructs (25-519GH, 25-932GH and 567-928GH) to immobilized heparin. Both full length MET (25-932GH) and MET 25-519GH showed binding while MET 567-928GH showed none. The strong heparin binding of mature (two-chain) HGF/SF is shown for comparison in FIG. 2c.

Immulon B 96 well plates were coated with recombinant, single chain (R494E) or two chain HGF/SF in 50 mM phosphate buffer, pH 6.0. Wells were blocked, incubated with dimeric MET constructs at the concentrations shown in FIGS. 2a and b and bound MET was detected with HRP-conjugated rabbit anti-human IgG (Dako P0214). For heparin binding, dimeric MET constructs were loaded on a HiTrap Heparin HP column (Amersham Biosciences 17-0406-01) in 50 mM phosphate, 150 mM NaCl, pH 7.4 and eluted with a linear gradient of NaCl as shown in FIGS. 2c and d.

Solution Behaviour of HGF/SF, MET and HGF-SF-MET Complexes by Gel Electrophoresis and Analytical Sedimentation.

Monomeric MET proteins were characterized by agarose gel electrophoresis in 10 g/l agarose gels in 50 mM MES, pH 6.7 for 4 hours at 50 mA. Analytical sedimentation experiments were performed in a Beckman Optima XL-A ultracentrifuge, using an An60 Ti rotor. Sedimentation velocity was at 20.0° C. and various speeds (30-52,000 rev/min). Only a single cell was used and this was scanned repeatedly. Data were analysed by the dc/dt method (17, 18) using the program DC/DT+(19) with partial specific volumes, and solvent density and viscosity calculated from their compositions with the program Sednterp (Hayes, D. B, Laue, T. & Philo, J.; from the RASMB software archive). Sets of 8-12 scans were analysed to give plots of g(s*) against $s^*_{20,w}$, where g(s*) is the amount of material (in $D_{280}$ units) sedimenting between s* and (s*+ δs*), where δs* is set as small as the data allow, and $s^*_{20,w}$ is the apparent sedimentation coefficient, corrected to water at 20° C. The scans were also fitted with models for either 1 or 2 components, calculating $s_{20,w}$ and $M_r$ (from s and a fitted diffusion coefficient, based upon the broadening of the boundary). Plots of the residuals between the absorbance calculated from the model, with the fitted parameters, against $s^*_{20,w}$ were made to allow assessment of the adequacy of the model fit.

Results

MET Deletions.

Membrane-bound MET is cleaved by furin between $R_{307}$ and $S_{308*}$ (30) yielding an extracellular α chain (aa 25 to 307) and a longer β chain (aa 308 to 1390) of which aa 308-932 are outside the membrane (4, 31) (FIG. 1a, top line). The β chain contains a short, cystine-rich sequence (aa 520-561) indicated as a black box in FIG. 1a. To map the ligand-binding domain, two sets of MET deletions were produced in the mouse myeloma line NS0 either as histidine-tagged (H), monomeric proteins or as fusions to the Fc region of the human γ1 antibody heavy chain yielding dimeric, histidine-tagged MET proteins (GH). Four shorter N-terminal deletions could not be expressed at measurable levels but a larger one (567-928) yielded stable MET proteins (FIG. 1a). A total of sixteen C-terminal deletions were generated, several of which are shown in FIG. 1a (sequence boundaries), FIG. 1b (DNA inserts) and FIG. 1c (protein expression). The highest levels of expression were seen either with the 25-519 constructs or with the larger proteins (25-932 and 25-838). Intermediate constructs (25-567, 25-656 and 25-741) were expressed at low levels especially as monomeric proteins (FIG. 1c). Differences in expression levels reflected the properties of the constructs and not bias in selection. Truncations of MET 25-519 (FIG. 1a) could not be expressed at detectable levels.

The First 519 aa of MET are Sufficient for Binding HGF/SF and Heparin.

Binding of dimeric MET deletions to single chain (R494E) or two-chain HGF/SF is shown in FIGS. 2a and b. There were no significant differences in MET binding to the two ligands. The strongest binding was observed with the longest constructs but binding of 25-519GH and 25-567GH was readily measurable. In contrast, construct 567-932GH showed no binding (FIGS. 2a and 2b). Thus the N-terminal part of the MET ectodomain (aa 25-519) is sufficient for binding HGF/SF, while the C-terminal part (aa 567-932) has no binding activity but increases binding to the N-terminal one (25-519). There is evidence that MET binds heparan sulphate proteoglycans (HSPGs) (32-34). Thus, three MET constructs were used to map the region of MET responsible. The full MET ectodomain (construct 25-932GH) bound immobilised heparin, albeit with lower apparent affinity than HGF/SF (FIG. 2c). Binding of 25-519GH was indistinguishable from full length MET (25-932GH). In contrast, MET567-928GH exhibited no binding (FIG. 2d). Thus both the HGF/SF and the HSPG binding sites are contained in aa 25-519 of MET.

HGF/SF-MET Complexes.

Figure 3:
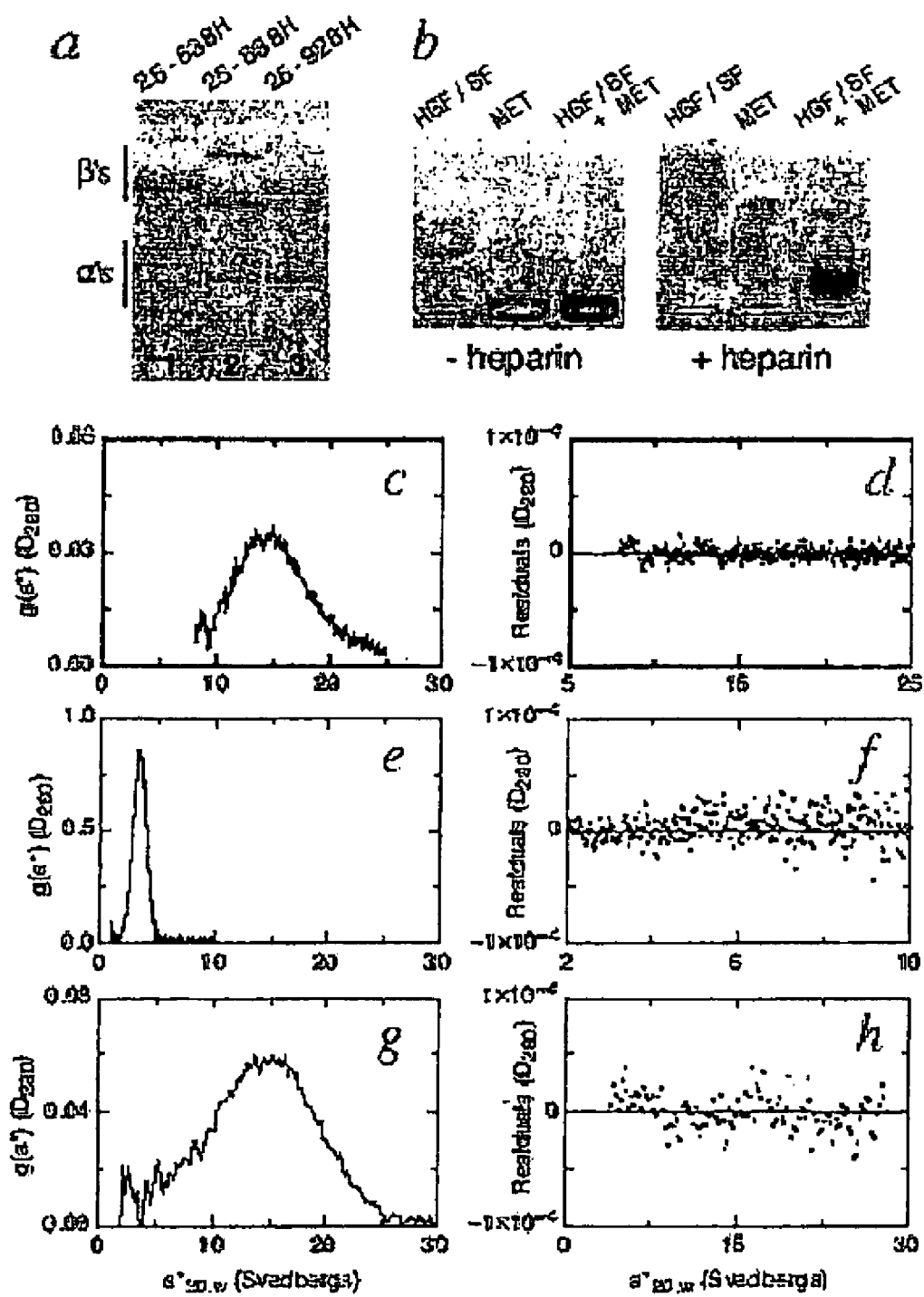
FIG. 3 shows monomeric full length MET and HGF/SF-MET complexes. a. SDS-PAGE under reducing conditions of MET 25-838H from NS0 (lane 1) or Lec 8 cells (lane 2) and MET 25-928H from Lec 8 cells. b. Gel electrophoresis under native conditions of HGF/SF, MET and HGF/SF-MET complexes in the absence or presence of heparin. c-h. Velocity sedimentation analysis of HGF/SF (c and d), MET (e and f) and the HGF/SFheparin-MET complex (g and h). c, e and g are plots of g(s*) against s*20,w , d, f and h are plots of the residuals, from fitting models to the data, against s*20,w on the right. Experiments shown in panels b, e and g were carried out with equimolar concentrations of HGF/SF and MET 25-928H derived from Lec 8 cells ($4 \times 10^{-6}$ M) and a 2.5 fold excess of heparin.

The availability of soluble, monomeric forms of the MET receptor enabled studies of its solution properties and HGF/SF binding. FIG. 3a shows SDS gel electrophoresis under reducing conditions of MET 25-838H expressed in NS0 (lane 1) or Lec 8 cells (lane 2). The increased mobility of the β and α chain bands in MET from Lec 8 cells is due to reduced glycosylation by Lec 8 as a result of a mutation in the UDP-Gal transporter. Lane 3 is MET 25-928H from Lec 8 cells. Binding of full length, monomeric MET to HGF/SF was studied by gel filtration (data not shown), native gel electrophoresis and velocity sedimentation. FIG. 3b shows the electrophoretic mobility of HGF/SF, MET and HGF/SF-MET complexes in the presence or absence of heparin. At pH 6.7, HGF/SF displayed anodic mobility while MET exhibited no mobility. Incubation of HGF/SF or MET with heparin resulted in HGF/SF- or MET-heparin complexes with increased negative charge. Incubation of HGF/SF and MET with or without heparin resulted in distinct HGF/SF-MET or HGF/SFheparin-MET complexes (FIG. 3b).

FIGS. 3c-h show the behaviour of HGF/SF (c and d), MET (e and f) and the HGF/SF-heparin-MET complex (g and h) analyzed by ultracentrifugation, with plots of g(s*) against $s^*_{20,w}$ on the left and plots of the residuals, from fitting models to the data, against $s^*_{20,w}$ on the right. Velocity sedimentation of HGF/SF alone showed a wide peak, which could not be fitted satisfactorily by a model with a single component, but required two components, of roughly similar optical density, with $s_{20,w}$ of 14.4!S and 17.7!S and $M_r$ of 74 kDa and 21 kDa respectively. The presence of two species of different $s_{20,w}$ values may reflect an equilibrium between structurally distinct forms, as seen with the homologue plasminogen which exists in 'open' and 'closed' conformations (35).

MET alone (FIG. 3e, f) showed a single, symmetric peak, with the data well fitted by a model for a single component with $s_{20,w}$=3.5 S and M=109 kDa (a value intermediate to calculated masses of 102.6 kDa and 117.0 kDa without and with core N-linked carbohydrates). This is a low sedimentation coefficient for the molecular mass and, together with a Stoke's radius of 56 A from gel filtration experiments (data not shown), indicates a non-globular, rod shape for the MET ectodomain. Velocity sedimentation analysis of the HGF/SF-MET complex showed a complex boundary which required at least two components in the model to produce a reasonable fit, implying that the binary HGF/SF-MET complex is unstable in solution under the conditions employed. In contrast, the HGF/SF-heparin-MET complex yielded a symmetrical peak (FIG. 3g), well fitted by a model with a single component with $s_{20,w}$=15.4 S and $M_r$=179 kDa (FIG. 3h). While this molecular mass is somewhat lower than that calculated for a 1:1:1 HGF/SFheparin-MET complex (~205 kDa), it is compatible only with such a complex and not with complexes of higher stoichiometries (2:1:2 or 2:2:2).

Discussion

Early cross-linking experiments indicated that HGF/SF binds to the MET β chain (5). The current study establishes that the first 519 aa of MET are required for HGF/SF binding which include the first 212 aa of the β chain. It is thus possible that the HGF/SF binding site is contained within this sequence. A heparin binding site also maps to the same region of MET (FIGS. 2c and d) and presumably mediates interactions with membranebound HSPG's.

A complex formed by HGF/SF, heparin and the whole MET ectodomain has a 1:1:1 stoichiometry in solution (FIG. 3g, h). Different crystal structures have shown receptor dimers complexed with bivalent ligand, (GH-GH receptor) (43) or dimeric ligand, (NGF-Trk) (42). Recent structures of truncated forms of the EGF receptor ectodomain complexed with EGF (44) or TGFα (45), however, have shown 2:2 complexes resulting from interactions between the two receptors and imply conversion from an inactive EGF receptor dimer into an active one. In essence, although dimerization or oligomerization may be general pre-requisite for activation of RTKs, a variety of structural mechanisms appear to be at work and the early suggestion that RTKs are activated by ligand-induced receptor-dimerization (46) may only apply to a subset of ligand-receptor pairs.

There are several mechanisms for MET dimerization compatible with the data reported here. Dimerization may depend on weak dimerization sequences within the ectodomain that operate at higher concentrations of ligand and receptor. Alternatively, it may rely on sequences within the trans- or juxtamembrane as in the neu receptor (47). Finally, it may depend on interactions with additional protein(s). There have been reports of selective association between MET and α6β4 integrin (48) and plexin B1 (49) and, while a critical role of α6β4 integrin for MET signalling is not supported by genetic studies in the mouse (50) (51), the possibility remains for plexin B1.

EXAMPLE 2

This example illustrates a solid phase assay showing binding of HGF/SF to MET.

MET928H protein at $2\times10^{-8}$ M in PBS (2 mg/l) was coated onto a 96 well Pierce Reacti-Bind™ plates, using 50 microliters per well. The plates were blocked with 20 g/l defatted milk (Marvel™) in PBS (200 microliters per well).

HGF/SF at concentrations ranging between $1\times10^{-7}$ and $1\times10^{-11}$ M diluted in blocking buffer were added to the wells as the second layer, followed by sheep anti-HGF/SF polyclonal antibody (1W53, diluted 1:1000 in blocking buffer. The fourth layer added was HRP-conjugated rabbit anti-sheep antibody (Dako P0163, 1:1000 in blocking buffer), followed by HRP substrate (ABTS, Sigma A-9941) to detect the amount of fourth layer bound. Absorbance at 415 nm ($A_{415}$) nm was measured for each concentration of HGF/SF used.

Figure 4:
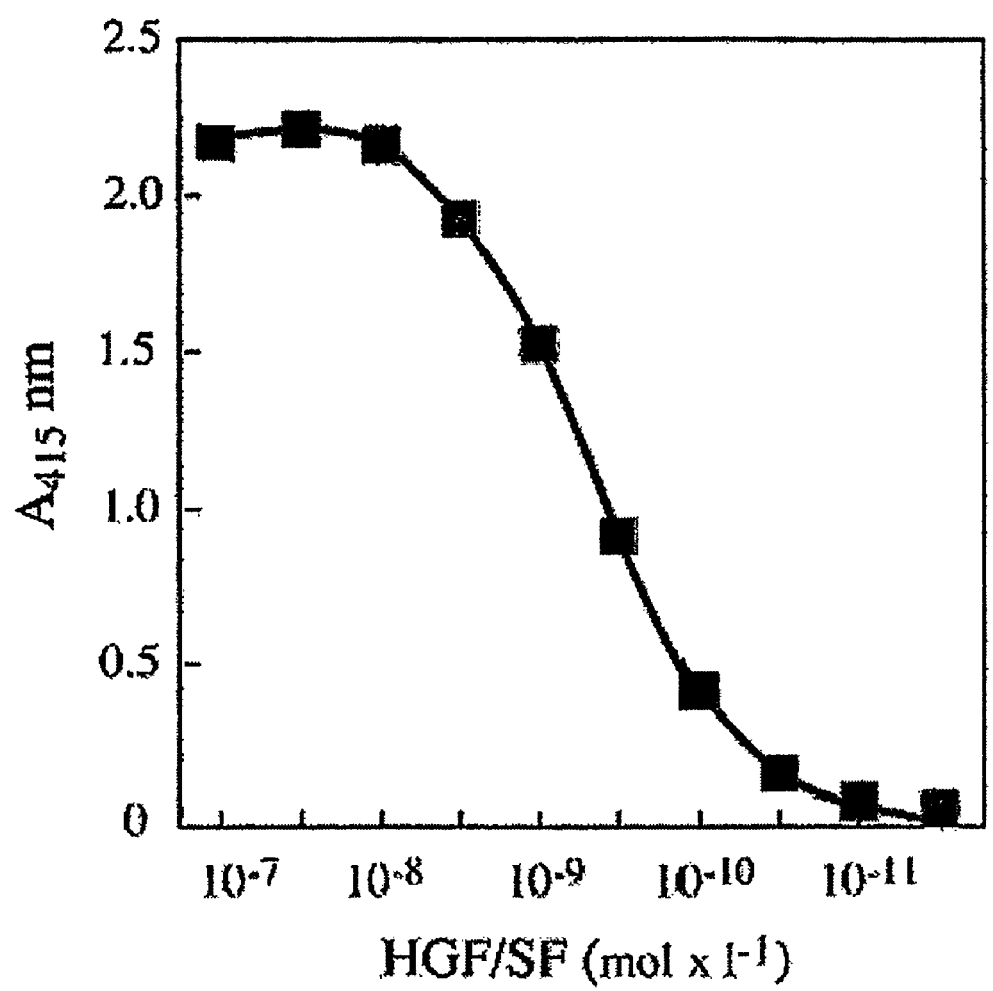
FIG. 4 shows the binding on HGF/SF to MET in a solid phase assay.

The results are shown in FIG. 4. This shows sensitive detection of binding of HGF/SF to MET under the conditions of the assay.

EXAMPLE 3

This example demonstrates an ELISA assay for HGF/SF interaction with biotinylated HGF/SF.

Preparation of Biotinyla ted HGF/SF

Purified HGF/SF (1 mg) was dialysed into reaction buffer 0.1M sodium acetate pH5.5 (RB). The dialysed protein was recovered in 0.66 ml RB and mixed with an equal volume of freshly-prepared 2 mM sodium periodate solution prepared in RB. The oxidation reaction was allowed to proceed for 30 min on ice in the dark. Oxidation was stopped by addition of glycerol to 15 mM final concentration to the reaction and the HGF/SF dialysed against RB to remove residual sodium periodate.

A 50 mM solution of biotin hydrazide (Pierce cat. No. 21340) was prepared freshly in dimethylsulfoxide (DMSO). A 1/10 volume of biotin hydrazide stock was added to the oxidised HGF/SF and allowed to react with mixing for 2 h at ambient temperature.

The product was dialysed against 50 mM MES pH6.7 containing 0.75M sodium chloride (MES/NaCl). Biotinylated HGF/SF was purified to remove un-reacted biotin by gel filtration chromatography using a Superdex 200 column fitted to the SMART chromatography apparatus (Amersham). Biotinylated HGF/SF was identified as a discrete peak and collected for use in the assay. Sodium azide was added to 0.05% as a preservative.

ELISA Assay for HGF/SF Interaction with Biotinylated HGF/SF

Purified MET protein (MET928H, 2-16 μg/ml, 50 μl per well) was used to coat either HisGrab nickel-coated (Pierce) or Maxisorp ELISA 96-well plates (Nunc) by dilution in 10 mM phosphate buffer containing 137 mM sodium chloride (PBS). Plates were incubated at 4° C. for 16 to 18 h.

The plates were washed 3× by aspiration of the well contents followed by filling and emptying with PBS containing 0.1% Tween 20 using an automated plate washer.

The plates were blocked by incubation with 100 μl per well PBS containing 3% bovine serum albumin (BSA)/(Sigma A-7906) for 1 h at ambient temperature. The plates were washed 3 times, as above.

Serial semi-log dilutions of biotinylated HGF/SF were prepared in PBS containing 2% w/v non-fat milk powder (Marvel™). The diluted reagent (50 μl/well) was incubated for 1 h at ambient temperature. The plates were again washed 3 times, as above.

A 1 mg/ml stock of streptavidin peroxidase conjugate (Pierce, 21126) was diluted 1/20,000 in PBS containing 1% w/v BSA and 50 μl added to all wells for 1 h at ambient temperature, and the plates washed 5 times. 3,3', 5,5', tetramethylbenzidine (TMB)/(Sigma T-2885) substrate solution was freshly prepared by adding 1/10 volume of a 1% w/v TMB stock in DMSO to the substrate buffer (0.1M sodium acetate buffer pH 4.5 containing 0.01% v/v hydrogen peroxide). Substrate solution (50 μl) was added to all wells and incubated for 20 min at ambient temperature. The reaction was stopped by addition of 12.5 μl/well of 1M sulphuric acid solution.

Figure 5:
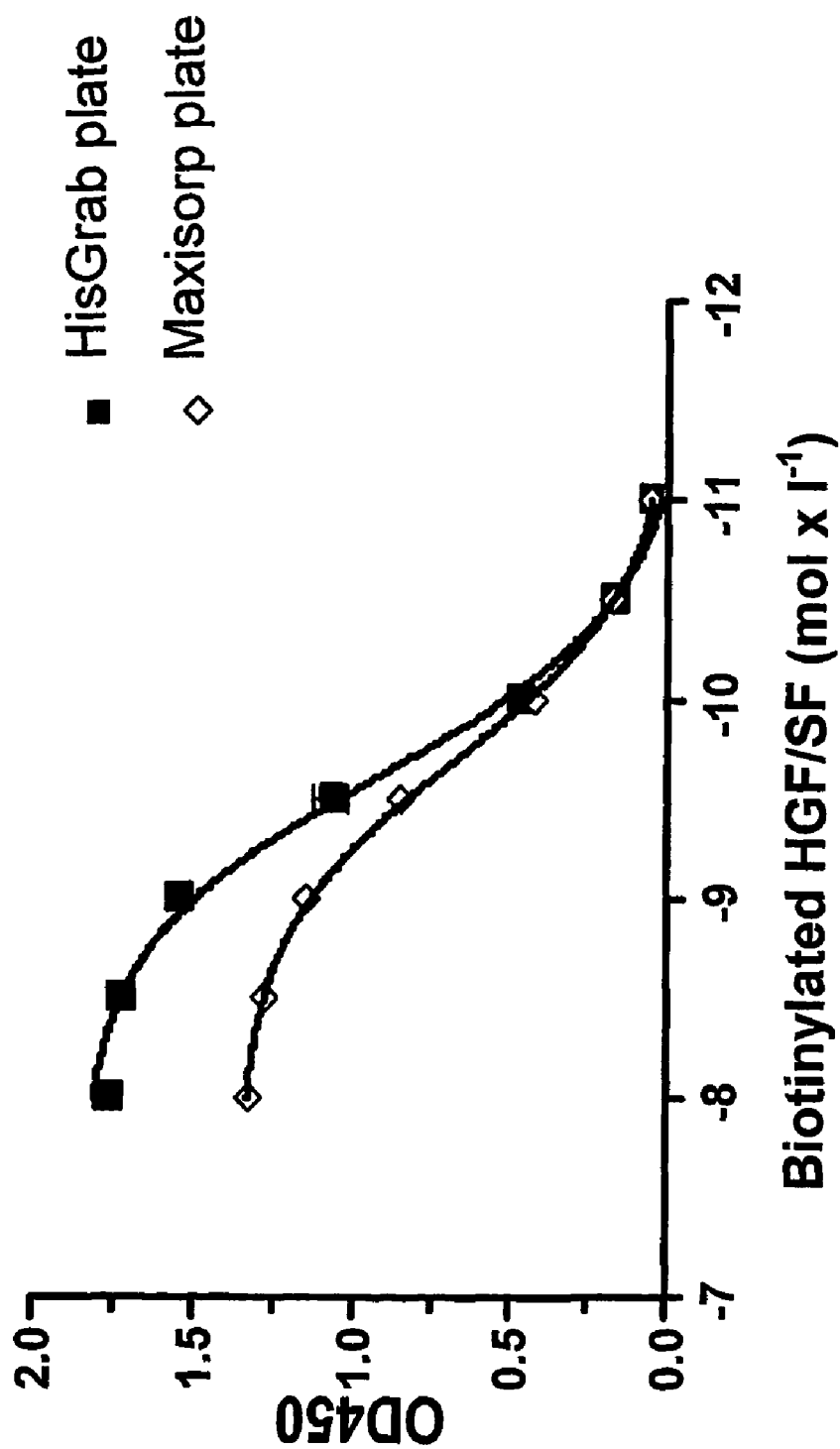
FIG. 5 shows a graph to illustrate binding of biotinylated HGF/SF to MET in an ELISA assay. MET was immobilised on either a HisGrab nickel-coated plate (Pierce) at 4 µg/ml or a Maxisorp plate (Nunc) at 8 µg/ml. The $EC_{50}$ values were $2.2 \times 10^{-10}$ mol $l^{-1}$ or $1.95 \times 10^{10}$ mol $l^{-1}$ or the HisGrab or Maxisorp plate respectively.

The absorbance at 450 nm was determined using a microplate reader (BioRad model 3550) with subtraction of reference absorbance wavelength (600 nm). The results are shown in FIG. 5, which illustrates that quantitative detection of binding in proportion to the concentration of HGF/SF is observed.

Accordingly, an assay of the invention may utilize a solid phase system of the type illustrated in Examples 2 and 3 in which a MET ectodomain of the invention is fixed to a solid phase and the extent to which it binds to HGF/SF (or fragments thereof) determined in the presence and absence of an agent. A person of skill in the art will appreciate that the precise details of the assay may be varied within routine experimental parameters—for example different components may be labelled and/or different antibodies or reagents may be substituted for those used in these examples.

EXAMPLE 4

The assay method of Example 3 was repeated as described, using a 384 well format in place of the 96 well format, using 400 ng of MET 928H per well.

The assay was scaled up to screen using a library of 10,000 chemical compounds (Maybridge, Cornwall, UK) plus 1,040 natural products. A final compound concentration of 20 μM per well was used.

The assay Z values (a measure of assay performance—see Zhang, J. H., Chung, T. D., and Oldenburg K. R. (1999) "A simple statistical parameter for use in evaluation and validation of high throughput screening assays" J. Biomol. Screening, 4, 67-73) were Z'=0.63, Z=0.55.

Figure 6:
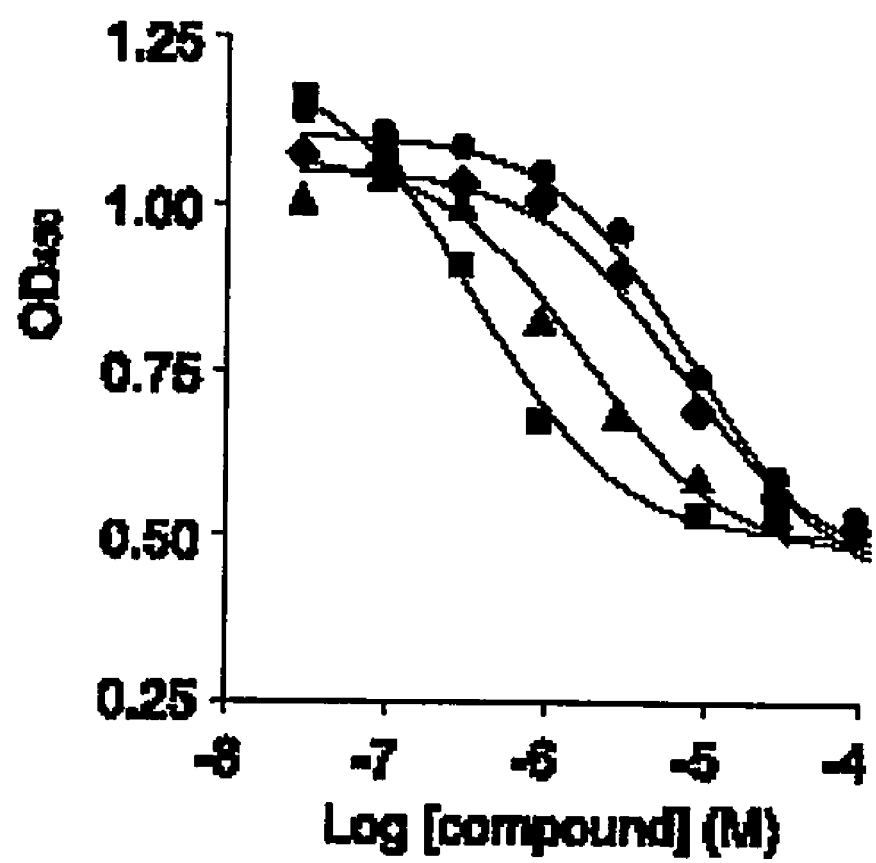
FIG. 6 shows the inhibition of binding of biotinylated HGF/SF to MET in an assay in the presence of a compound positive from a library screen plus three others identified from sub-structure searching.
Figure 7:
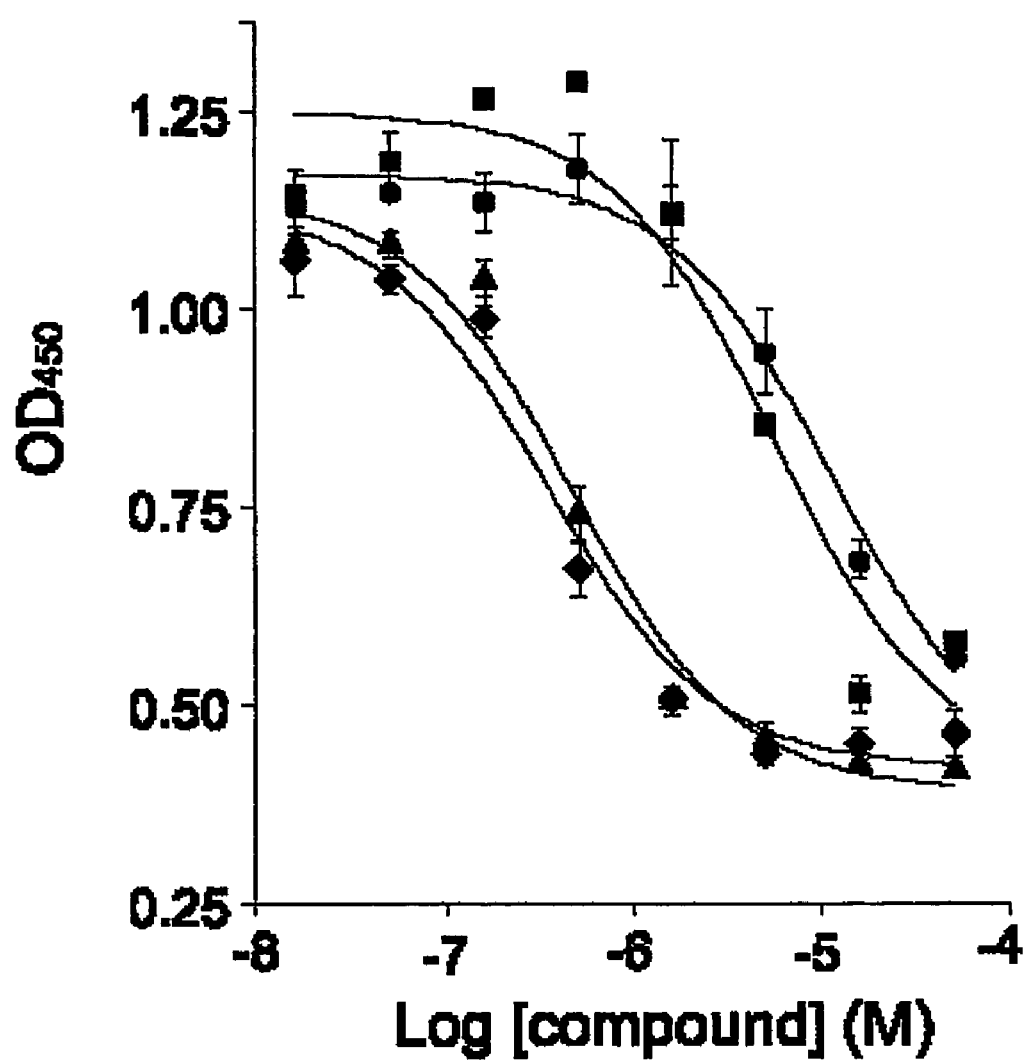
FIG. 7 shows the inhibition of binding of biotinylated HGF/SF to MET in an assay in the presence of a compound positive from a library screen plus three others identified from sub-structure searching.

The assay provided a confirmed hit rate of 0.44%, as judged by the criteria of reducing binding of HGF/SF to MET by 20% or more. Two of the compounds from the library were used for sub-structure searching to identify related active compounds. FIGS. 6 and 7 each illustrate the absorbance at 450 nm detected as an indication of HGF/SF binding to the plates in the presence of a range of concentrations of a hit compound plus three sub-structure compounds.

The activity of the hit compounds was also confirmed by an MDCK scatter assay, performed as described by Stoker et al, 1987 [Ref. 6]. Briefly, the effect of HGF/SF on colony expansion of the canine kidney epithelial cell line MDCK is determined, using $10^{-11}$ M HGF/SF in the presence or absence of a hit compound at a concentration of $3 \times 10^{-5}$ M. The compound was addedd to 5,000 MDCK cells in 0.3 ml of 5% Fetal Bovine Serum in DMEM in 96 well plates and incubated overnight at 37° C. in 5% $CO_2$ incubator. The following morning the plates were fixed for 5 minutes in 10% formaldehyde and stained in a solution of 2% Coomassie Brilliant Blue in water/methanol/acetic acid (50/40/10) before photography. The compound was observed to inhibit colony scattering.

REFERENCES

1. Blume-Jensen, P. & Hunter, T. (2001) Nature 411, 355-65.
2. Harpaz, Y. & Chothia, C. (1994) J Mol Biol 238, 528-39.
3. Cooper, C. S., Blair, D. G., Oskarsson, M. K., Tainsky, M. A., Eader, L. A. & Vande Woude, G. F. (1984) Cancer Res 44, 1-10.
4. Park, M., Dean, M., Kaul, K., Braun, M. J., Gonda, M. A. & Vande Woude, G. (1987) Proc Natl Acad Sci U S A 84, 6379-83.

5. Bottaro, D. P., Rubin, J. S., Faletto, D. L., Chan, A. M., Kmiecik, T. E., Vande Woude, G. F. & Aaronson, S. A. (1991) Science 251, 802-4.
6. Stoker, M., Gherardi, E., Perryman, M. & Gray, J. (1987) Nature 327, 239-42.
7. Gherardi, E., Gray, J., Stoker, M., Perryman, M. & Furlong, R. (1989) Proc Natl Acad Sci U S A 86, 5844-8.
8. Nakamura, T., Nishizawa, T., Hagiya, M., Seki, T., Shimonishi, M., Sugimura, A., Tashiro, K. & Shimizu, S. (1989) Nature 342, 440-3.
9. Miyazawa, K., Tsubouchi, H., Naka, D., Takahashi, K., Okigaki, M., Arakaki, N., Nakayama, H., Hirono, S., Sakiyama, O. & et al. (1989) Biochem Biophys Res Commun 163, 967-73.
10. Zarnegar, R. & Michalopoulos, G. (1989) Cancer Res 49, 3314-20.
11. Schmidt, C., Bladt, F., Goedecke, S., Brinkmann, V., Zschiesche, W., Sharpe, M., Gherardi, E. & Birchmeier, C. (1995) Nature 373, 699-702.
12. Uehara, Y., Minowa, O., Mori, C., Shiota, K., Kuno, J., Noda, T. & Kitamura, N. (1995) Nature 373, 702-5.
13. Bladt, F., Riethmacher, D., Isenmann, S., Aguzzi, A. & Birchmeier, C. (1995) Nature 376, 768-71.
14. Schmidt, L., Duh, F. M., Chen, F., Kishida, T., Glenn, G., Choyke, P., Scherer, S. W., Zhuang, Z., Lubensky, I., Dean, M., Allikmets, R., Chidambaram, A., Bergerheim, U. R., Feltis, J. T., Casadevall, C., Zamarron, A., Bernues, M., Richard, S., Lips, C. J., Walther, M. M., Tsui, L. C., Geil, L., Orcutt, M. L., Stackhouse, T., Zbar, B. & et al. (1997) Nat Genet 16, 68-73.
15. Comoglio, P. M. (2001) Nat Cell Biol 3, E161-2.
16. Oelmann, S., Stanley, P. & Gerardy-Schahn, R. (2001) J Biol Chem 276, 26291-300.
17. Stafford, W. F., 3rd (1992) Anal Biochem 203, 295-301.
18. Stafford, W. F., 3rd (1994) Methods Enzymol 240, 478-501.
19. Philo, J. S. (2000) Anal Biochem 279, 151-63.
20. Kelley, L. A., MacCallum, R. M. & Sternberg, M. J. (2000) J Mol Biol 299, 499-520.
21. Shi, J., Blundell, T. L. & Mizuguchi, K. (2001) J Mol Biol 310, 243-57.
22. Karplus, K., Barrett, C. & Hughey, R. (1998) Bioinformatics 14, 846-56.
23. Thompson, J. D., Higgins, D. G. & Gibson, T. J. (1994) Nucleic Acids Res 22, 4673-80.
24. Gough, J., Karplus, K., Hughey, R. & Chothia, C. (2001) J Mol Biol 313, 903-19.
25. Mizuguchi, K., Deane, C. M., Blundell, T. L. & Overington, J. P. (1998) Protein Sci 7, 2469-71.
26. Sali, A. & Blundell, T. L. (1993) J Mol Biol 234, 779-815.
27. Laskowski, R., MacArthur, M., Moss, D. & Thornton, J. M. (1993) J Appl Cryst 26, 283-291.
28. Luthy, R., Bowie, J. U. & Eisenberg, D. (1992) Nature 356, 83-5.
29. Sutcliffe, M. J., Hayes, F. R. & Blundell, T. L. (1987) Protein Eng 1, 385-92.
30. Komada, M., Hatsuzawa, K., Shibamoto, S., Ito, F., Nakayama, K. & Kitamura, N. (1993) FEBS Lett 328, 25-9.
31. Giordano, S., Ponzetto, C., Di Renzo, M. F., Cooper, C. S. & Comoglio, P. M. (1989) Nature 339, 155-6.
32. Rubin, J. S., Day, R. M., Breckenridge, D., Atabey, N., Taylor, W. G., Stahl, S. J., Wingfield, P. T., Kaufman, J. D., Schwall, R. & Bottaro, D. P. (2001) J Biol Chem 276, 32977-83.
33. Lietha, D., Chirgadze, D. Y., Mulloy, B., Blundell, T. L. & Gherardi, E. (2001) Embo J 20, 5543-55.
34. Lyon, M., Deakin, J. A. & Gallagher, J. T. (2002) J Biol Chem 277, 1040-6.
35. Mangel, W. F., Lin, B. H. & Ramakrishnan, V. (1990) Science 248, 69-73.
36. Winberg, M. L., Noordermeer, J. N., Tamagnone, L., Comoglio, P. M., Spriggs, M. K., Tessier-Lavigne, M. & Goodman, C. S. (1998) Cell 95, 903-16.
37. Bork, P., Doerks, T., Springer, T. A. & Snel, B. (1999) Trends Biochem Sci 24, 261-3.
38. Xiong, J. P., Stehle, T., Diefenbach, B., Zhang, R., Dunker, R., Scott, D. L., Joachimiak, A., Goodman, S. L. & Arnaout, M. A. (2001) Science 294, 339-45.
39. Cuff, J. A. & Barton, G. J. (2000) Proteins 40, 502-11.
40. Lo Conte, L., Ailey, B., Hubbard, T. J., Brenner, S. E., Murzin, A. G. & Chothia, C. (2000) Nucleic Acids Res 28, 257-9.
41. Pellegrini, L., Burke, D. F., von Delft, F., Mulloy, B. & Blundell, T. L. (2000) Nature 407, 1029-34.
42. Wiesmann, C., Ultsch, M. H., Bass, S. H. & de Vos, A. M. (1999) Nature 401, 184-8.
43. de Vos, A. M., Ultsch, M. & Kossiakoff, A. A. (1992) Science 255, 306-12.
44. Ogiso, H., Ishitani, R., Nureki, O., Fukai, S., Yamanaka, M., Kim, J. H., Saito, K., Sakamoto, A., Inoue, M., Shirouzu, M. & Yokoyama, S. (2002) Cell 110, 775-87.
45. Garrett, T. P., McKern, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W. & Ward, C. W. (2002) Cell 110, 763-73.
46. Ullrich, A. & Schlessinger, J. (1990) Cell 61, 203-12.
47. Bargmann, C. I., Hung, M. C. & Weinberg, R. A. (1986) Cell 45, 649-57.
48. Trusolino, L., Bertotti, A. & Comoglio, P. M. (2001) Cell 107, 643-54.
49. Giordano, S., Corso, S., Conrotto, P., Artigiani, S., Gilestro, G., Barberis, D., Tamagnone, L. & Comoglio, P. M. (2002) Nat Cell Biol 4, 720-4.
50. Georges-Labouesse, E., Messaddeq, N., Yehia, G., Cadalbert, L., Dierich, A. & Le Meur, M. (1996) Nat Genet 13, 370-3.
51. van der Neut, R., Krimpenfort, P., Calafat, J., Niessen, C. M. & Sonnenberg, A. (1996) Nat Genet 13, 366-9.
52. Jawad, Z. & Paoli, M. (2002) Structure (Camb) 10, 447-54.
53. Cioce, V., et al (1996). Hepatocyte growth factor (HGF)/NK1 is a naturally occurring HGF/scatter factor variant with partial agonist/antagonist activity, J Biol Chem 271, 13110-5.
54. Chan, A. M., et al (1991). Identification of a competitive HGF antagonist encoded by an alternative transcript, Science 254, 1382-5.
55. Hartmann, G., et al (1992). A functional domain in the heavy chain of scatter factor/hepatocyte growth factor binds the c-Met receptor and induces cell dissociation but not mitogenesis, Proc Natl Acad Sci USA 89, 11574-8.
56. Jakubczak, J. L., et al (1998). NK1, a natural splice variant of hepatocyte growth factor/scatter factor, is a partial agonist in vivo, Mol Cell Biol 18, 1275-83.

The invention claimed is:

1. An assay method for determining whether an agent binds to a MET ectodomain fragment in monomeric form or for determining whether said agent disrupts binding of said ectodomain fragment to hepatocyte growth factor/scatter factor (HGF/SF) or for determining whether said agent disrupts the binding of said ectodomain fragment to a fragment of HGF/SF which otherwise binds said ectodomain which comprises:
    (a) providing a MET ectodomain fragment in monomeric form, wherein said MET is SEQ ID NO: 1 or the A320V variant thereof and wherein said MET ectodomain fragment comprises amino acids 25-928 of the MET ectodomain or is an N-terminal fragment of amino acids 25-928 of the MET ectodomain having 495 amino acids;
    (b) providing an agent; and
    (c) determining whether the agent binds to said fragment or disrupts the binding of said fragment to hepatocyte growth factor/scatter factor (HGF/SF) or a fragment of HGF/SF which binds to said ectodomain, wherein said HGF/SF is human HGF/SF recorded as SEQ ID NO: 2.

2. An assay according to claim 1 which is performed in the presence of HGF/SF or a fragment thereof which binds to said ectodomain.

3. An assay according to claim 1 which is performed in the presence of heparin or heparan sulphate.

4. An assay according to claim 1 wherein the MET ectodomain fragment is a fragment selected from amino acids 25-519, 25-567, 25-656, 25-741, and 25-838 of the MET ectodomain.

5. An assay according to claim 1 wherein the determining step (c) examines the extent to which the MET ectodomain fragment is dimerized in the presence of the agent.

6. An assay according to claim 1 wherein the assay is performed using gel electrophoresis, gel filtration or ultracentrifugation.

7. An assay according to claim 1 which is a solid phase binding assay.

8. An isolated MET ectodomain fragment in monomeric form, wherein said MET is SEQ ID NO: 1 or the A320V variant thereof and wherein said MET ectodomain fragment consists of amino acids 25-928 of the MET ectodomain or is an N-terminal fragment of amino acids 25-928 of the MET ectodomain having 495 amino acids.

9. An isolated MET ectodomain fragment in monomeric form, wherein said MET is SEQ ID NO: 1 or the A320V variant thereof and wherein said MET ectodomain fragment consists of amino acids 25-519, 25-567, 25-656, 25-741 or 25-838 of said MET.

10. A detectable MET ectodomain fragment comprising the fragment according to claim 8 and a detectable tag.

11. A composition comprising a MET ectodomain fragment of claim 8 together with a diluent or carrier.

12. A composition according to claim 11 which further comprises HGF/SF or a fragment thereof which binds to said ectodomain.

13. An composition according to claim 11 which further comprises heparin or heparan sulphate.

* * * * *